United States Patent [19]

Inglot et al.

[11] Patent Number: 5,543,300
[45] Date of Patent: Aug. 6, 1996

[54] METHOD AND COMPOSITION FOR DETERMINING THE IMMUNOLOGICAL ACTIVITY OF BIOACTIVE SUBSTANCES

[75] Inventors: Anna Inglot; Zofia Blach-Olszewska, both of Wroclaw, Poland

[73] Assignee: Torf Establishment, Liechtenstein

[21] Appl. No.: 211,909

[22] PCT Filed: Sep. 28, 1992

[86] PCT No.: PCT/EP92/02228

§ 371 Date: Apr. 26, 1994

§ 102(e) Date: Apr. 26, 1994

[87] PCT Pub. No.: WO93/08470

PCT Pub. Date: Apr. 29, 1993

[30] Foreign Application Priority Data

Oct. 26, 1991 [EP] European Pat. Off. .............. 91118269

[51] Int. Cl.$^6$ .............................. C12Q 1/02; C07K 14/52; C07K 14/525; A61K 35/78
[52] U.S. Cl. .............................. 435/29; 435/4; 530/351; 424/85.1; 424/195.1
[58] Field of Search ....................... 435/4, 29; 530/351; 424/85.1, 195.1

[56] References Cited

U.S. PATENT DOCUMENTS

| | | | |
|---|---|---|---|
| 5,096,708 | 3/1992 | Gohla et al. | 424/195.1 |
| 5,290,554 | 3/1994 | Tolpa et al. | 424/195.1 |

FOREIGN PATENT DOCUMENTS

| | | |
|---|---|---|
| 0227335 | 7/1987 | European Pat. Off. . |
| 0238851 | 9/1987 | European Pat. Off. . |
| 636448 | 5/1983 | Switzerland . |
| 8705400 | 9/1987 | WIPO . |

OTHER PUBLICATIONS

Martindale: The Extra Pharmacopoeia Ed: Reynolds pp. 257–261.

Cembrzynska–Nowak et al. "Hyporesponsiveness of Human Alvcolar Leukocytes to Interferon–Alpha & Interferon–Gamma Inducers" Immunobiol. 181 84–96 1990.

Gregg et al. "The Effect of Macrophage Activation State on Antigen Presenting Capability As Defined By Helper T–Cell Function" Int. J. Immunopharmac. 13(2B) 217–225 1991.

Czyrski et al. "Mitogenic Activity of Seleno Organic Compounds In Human Peripheral Blood Lymphocytes" Experientia 47 95–97 1991.

A. D. Inglot et al., Experientia, vol. 46, No. 3, 15 Mar. 1990, Basel CH, pp. 308–311, "Organoselenides as Potential Immunostimulatns and Inducers of Interferon Gamma and Other cytokines in Human Peripheral Blood Teukocytes".

Biological Abstracts, vol. 83, No. 3, 1987 Philadelphia, PA US., Ahmed Hamied, T. A. et al. "Potentiating Release of Interleukin–2 by Bleomycin", 1.

Biological Abstracts, vol. 91., No. 11, 1 Jun. 1991, Philadelphia, PA, US, Abstract No. 119260, M. Stein et al., "Regulation of TNF Release by Murine Peritoneal Macrophages".

(List continued on next page.)

Primary Examiner—Mindy Fleisher
Assistant Examiner—Nancy J. Degen
Attorney, Agent, or Firm—Ostrolenk, Faber, Gerb & Soffen, LLP

[57] ABSTRACT

The immunological activity of certain bioactive substances is determined by treating a human peripheral blood leukocyte (PBL) culture or a suspension of BALB/c mice resident peritoneal cells (RPC), with a solution of the substance to be tested in order to induce production of cytokines which then are determined according to standard identification methods; amplification of the results may be achieved by admixing, to the solution to be tested, a non-steroidal anti-inflammatory drug, preferably indomethacin. The method is also useful for determining the immunological response of a human individual to a therapy using a cytokine inducing substance.

25 Claims, 11 Drawing Sheets

OTHER PUBLICATIONS

The Journal of Immunology, vol. 139, No. 3, 1 Aug. 1987, Baltimore, MD. US. pp. 899–904, H. Kriegbaum et al. "Correlation of Immunogenicity and Production of Ornithine by Peritoneal Macrophage".

A. D. Inglot, et al., Chemical Abstracts, vol. 100, No. 17, 23 Apr. 1984, Columbus, OH, US; Abstract No. 132148, "Antiviral Activity of Wratizolin", Arch. Immunol. Ther. Exp. 1983, 31(5), 601–10.

E. Romanowska et al., Chemical Abstracts, vol. 100, No. 17, 13 Apr. 1984, Columbus, OH, US; Abstract No. 132009, "Interaction of Wratizolin with Serum Albumins and Its Antproteolitic Activity", p. 10 & Arch. Immunol. Ther. Exp. 1983, 31(5), 583–91.

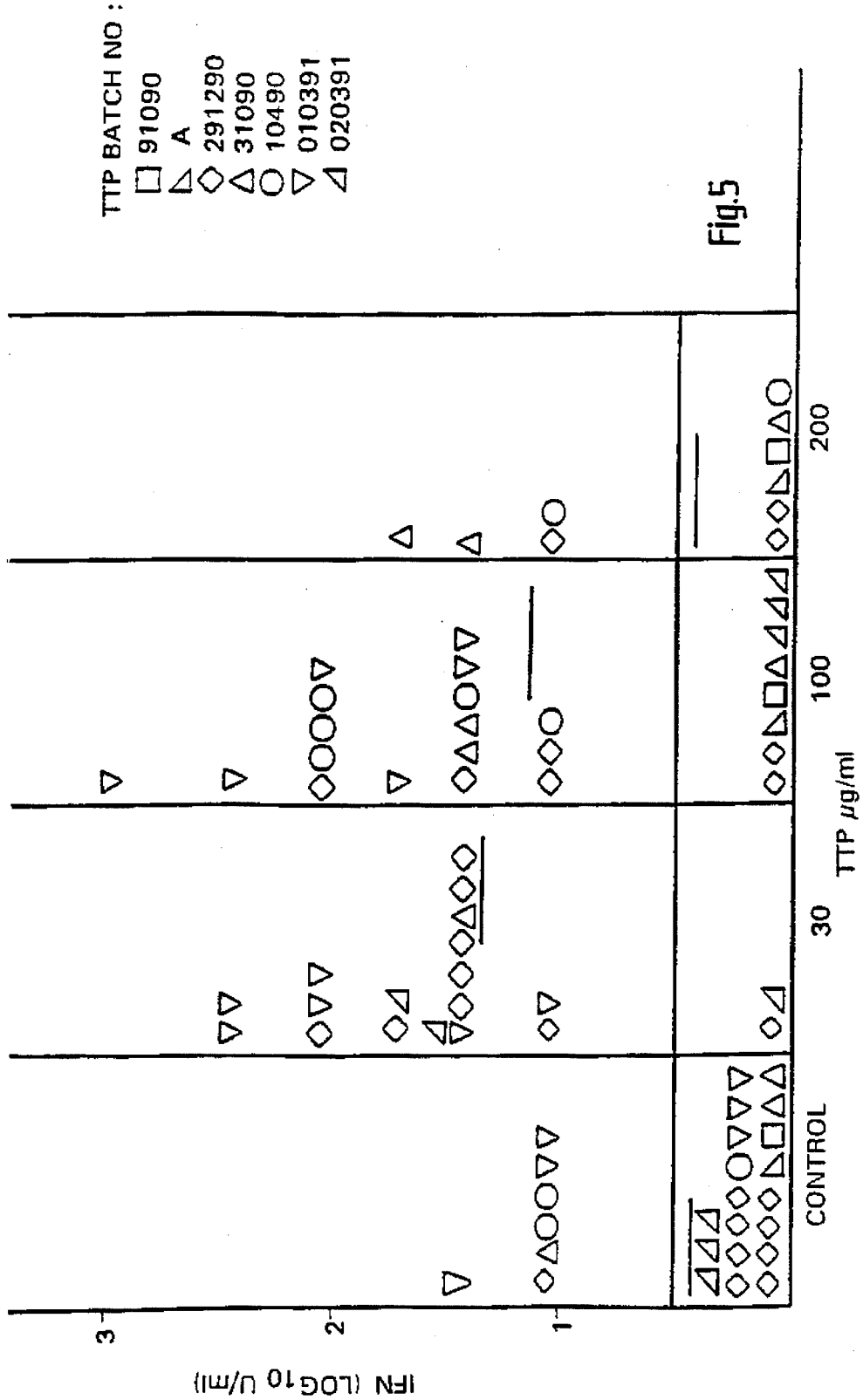

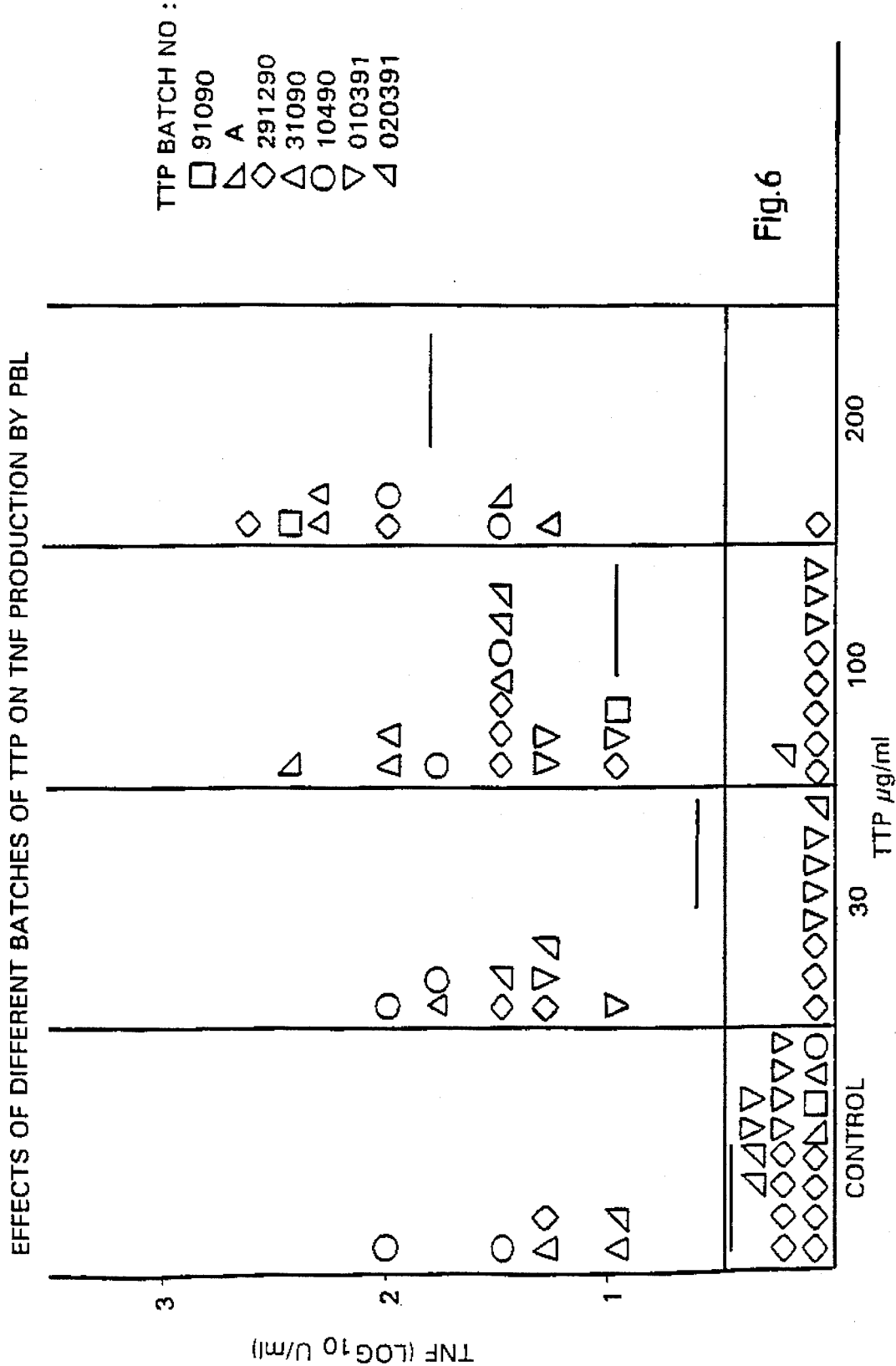

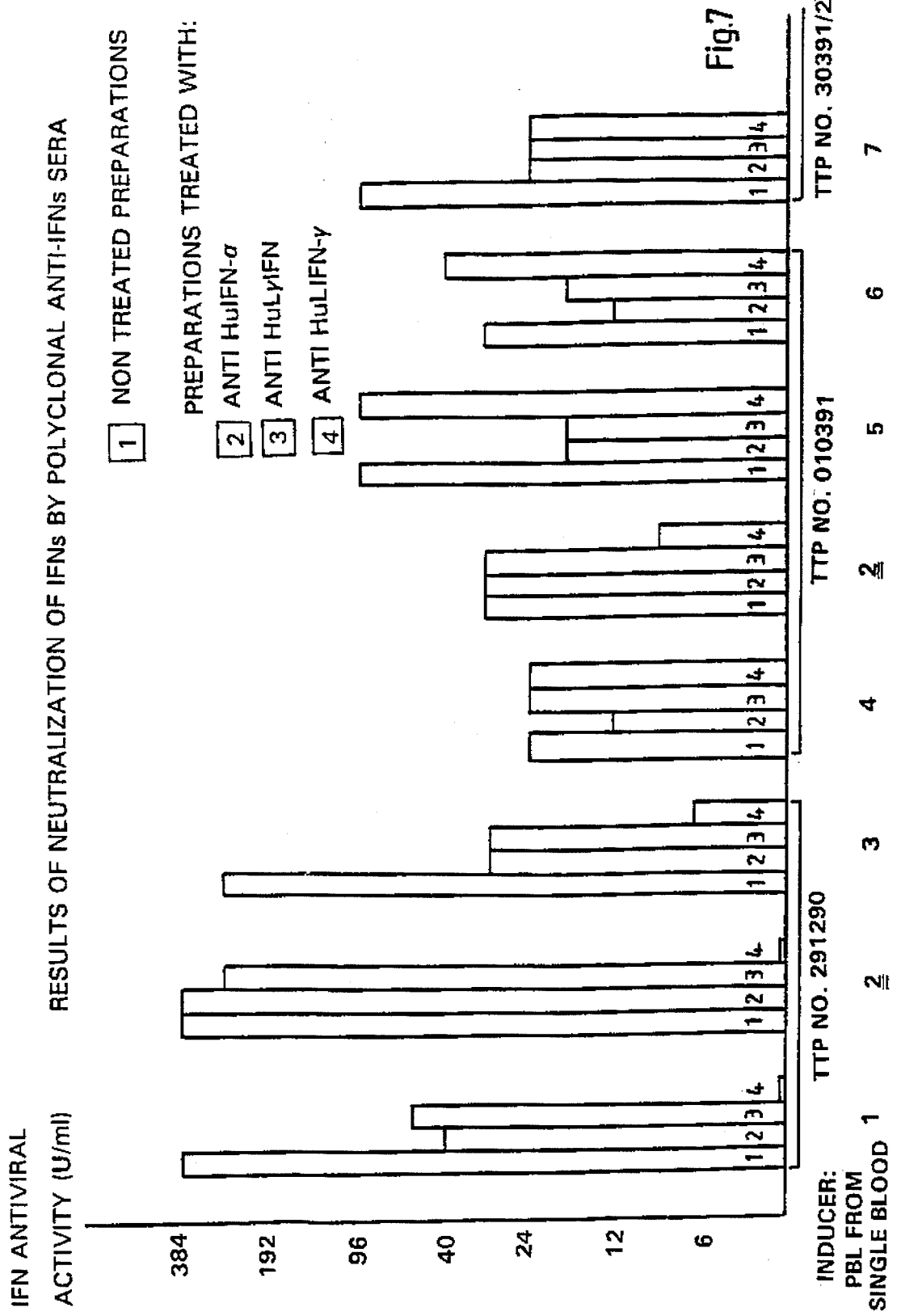

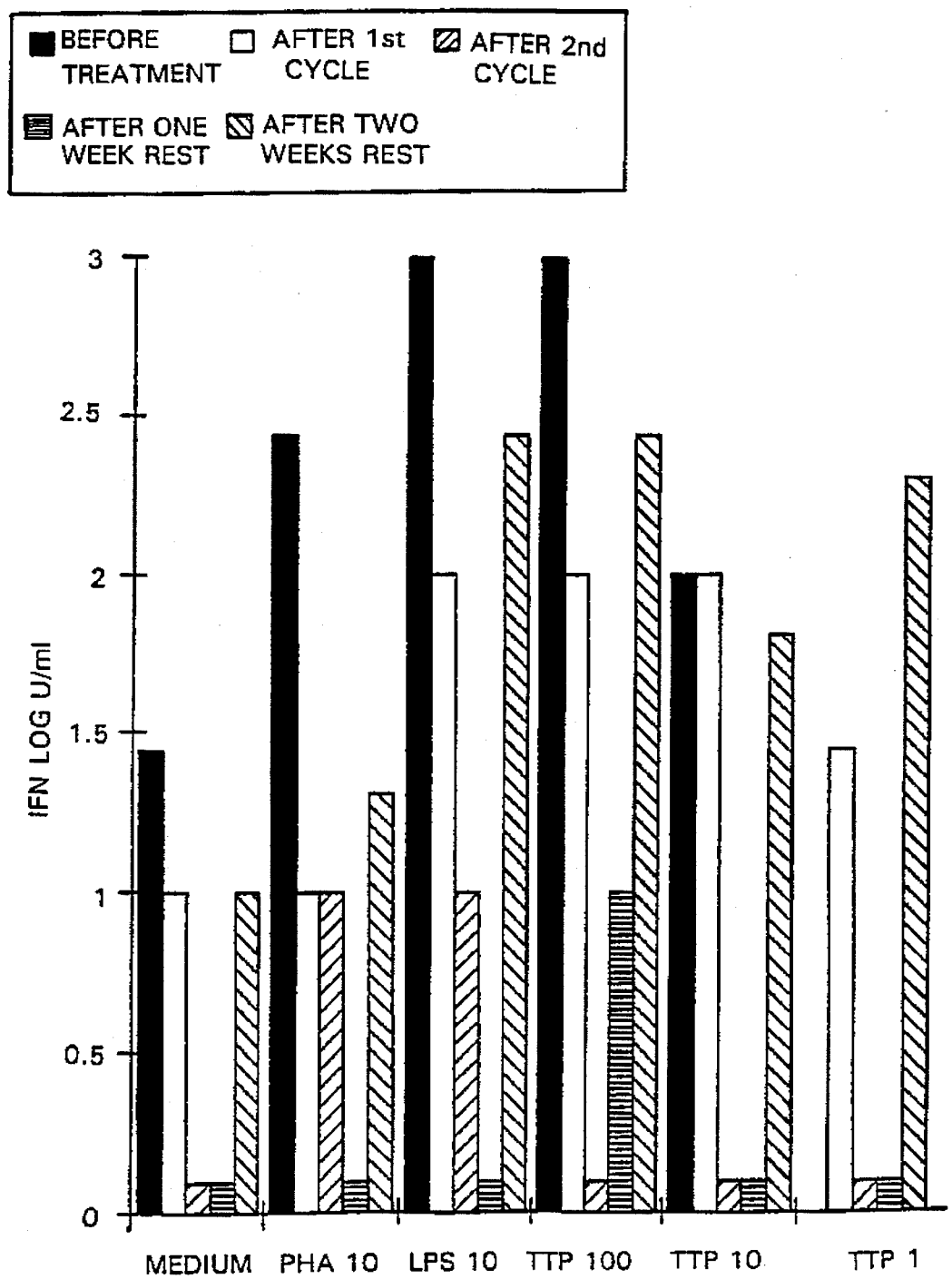

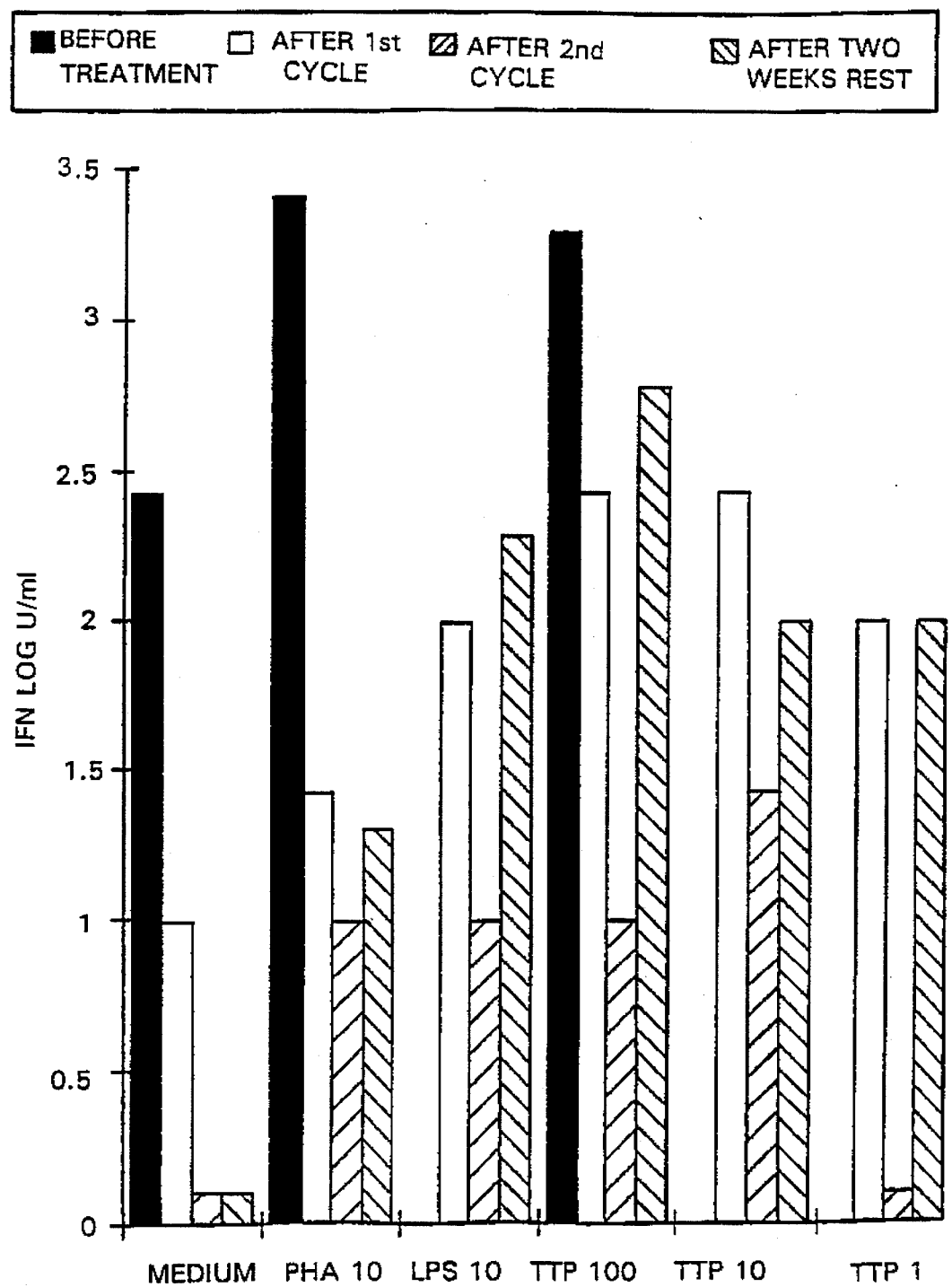

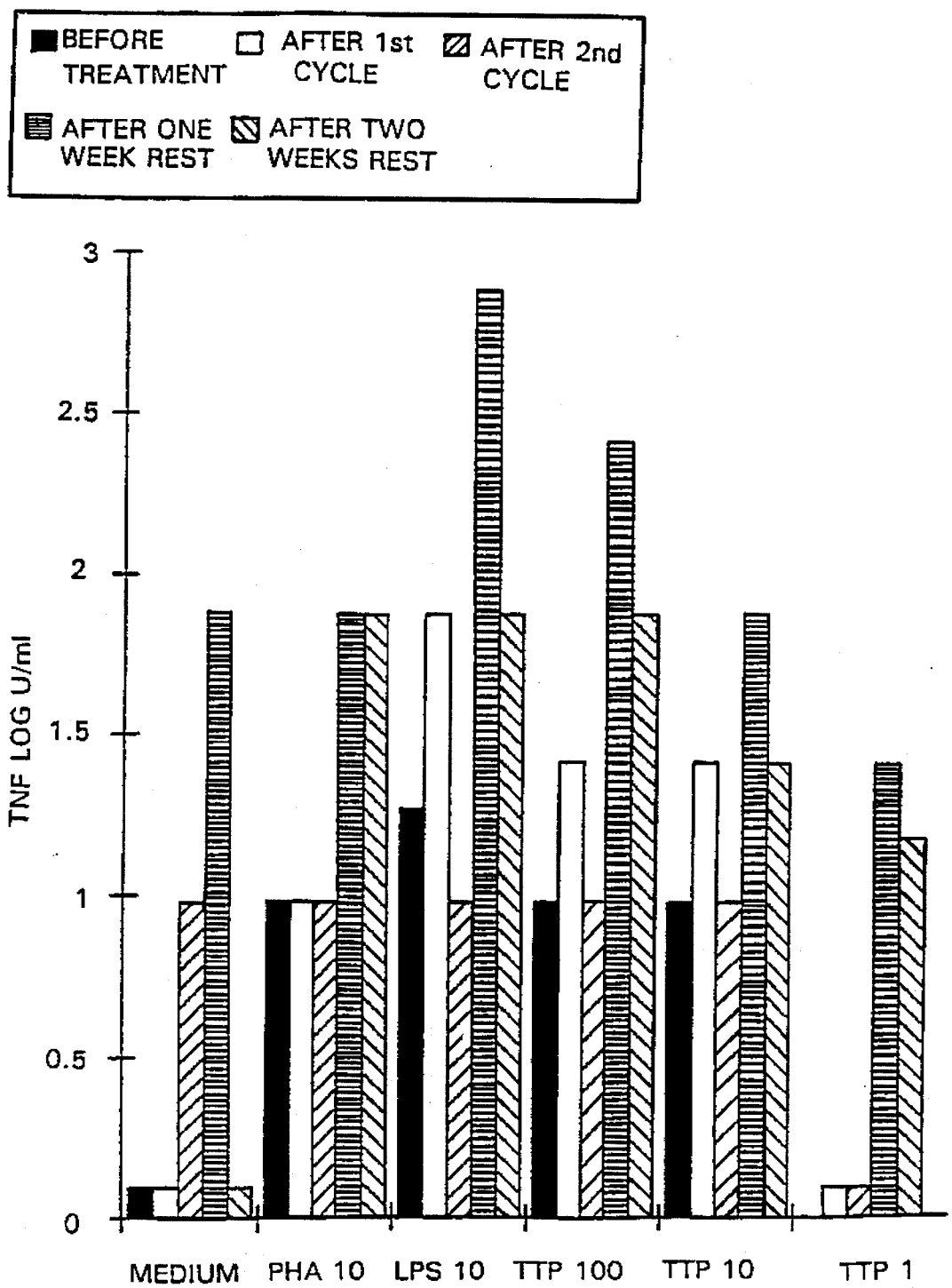

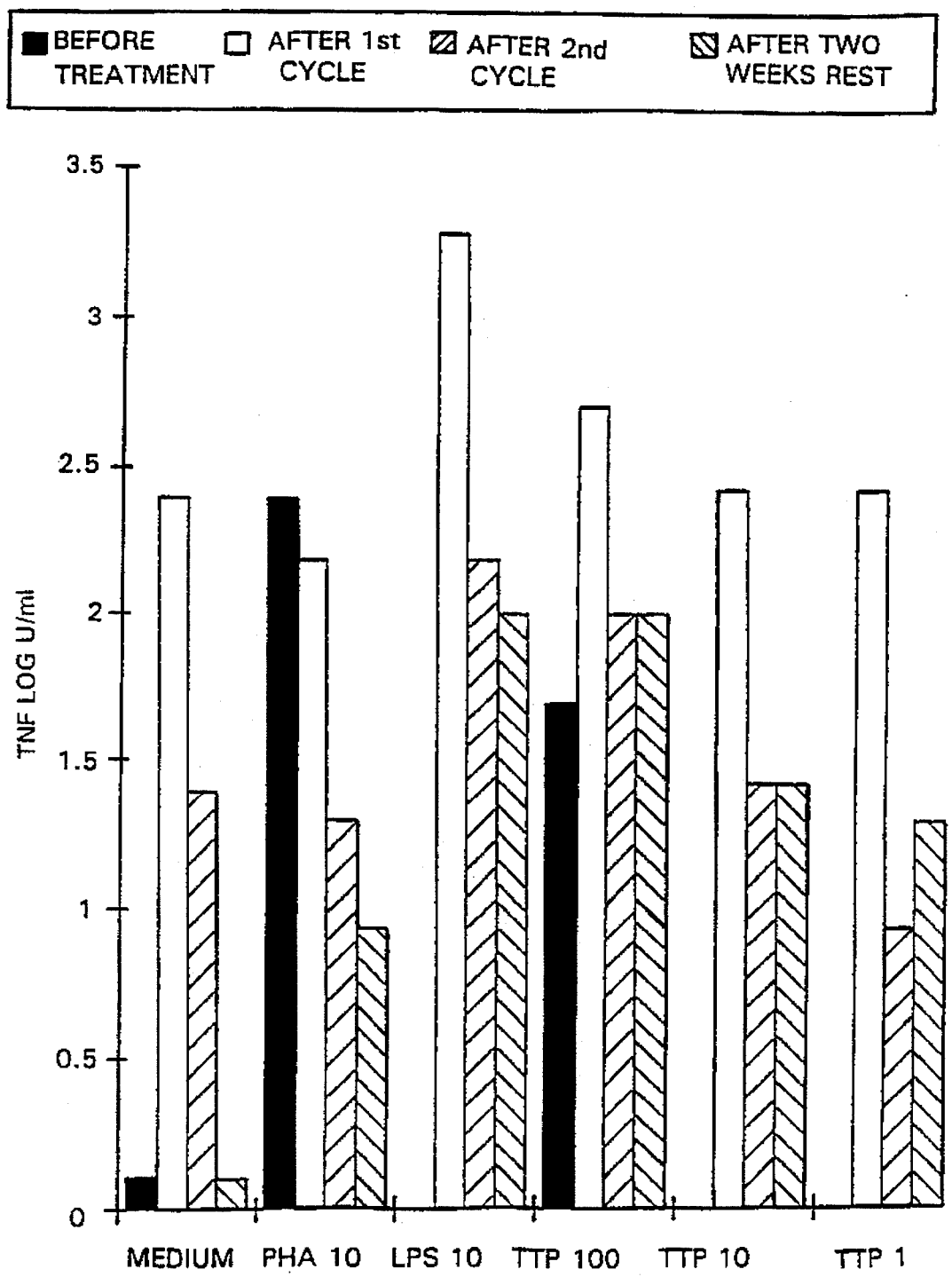

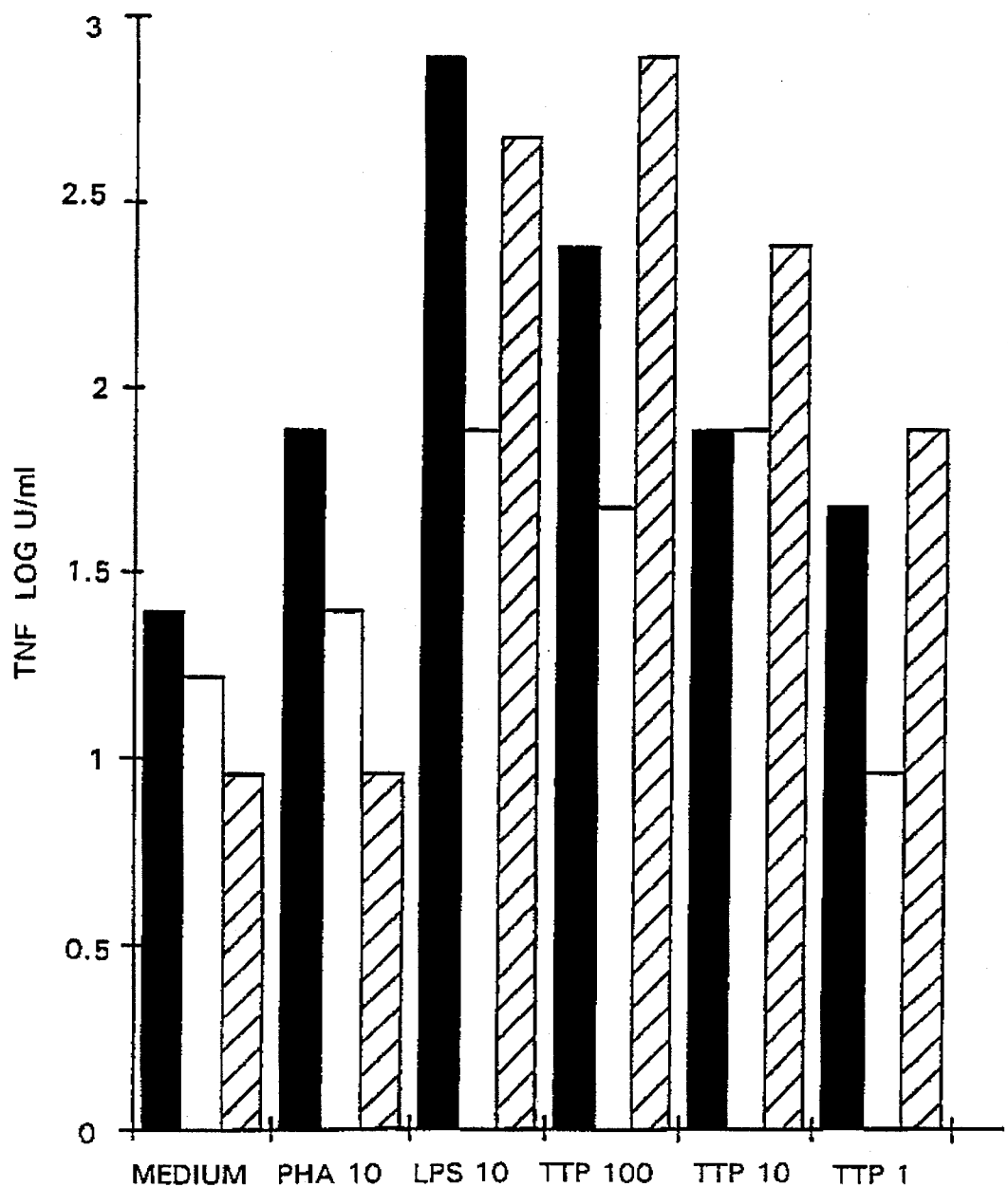

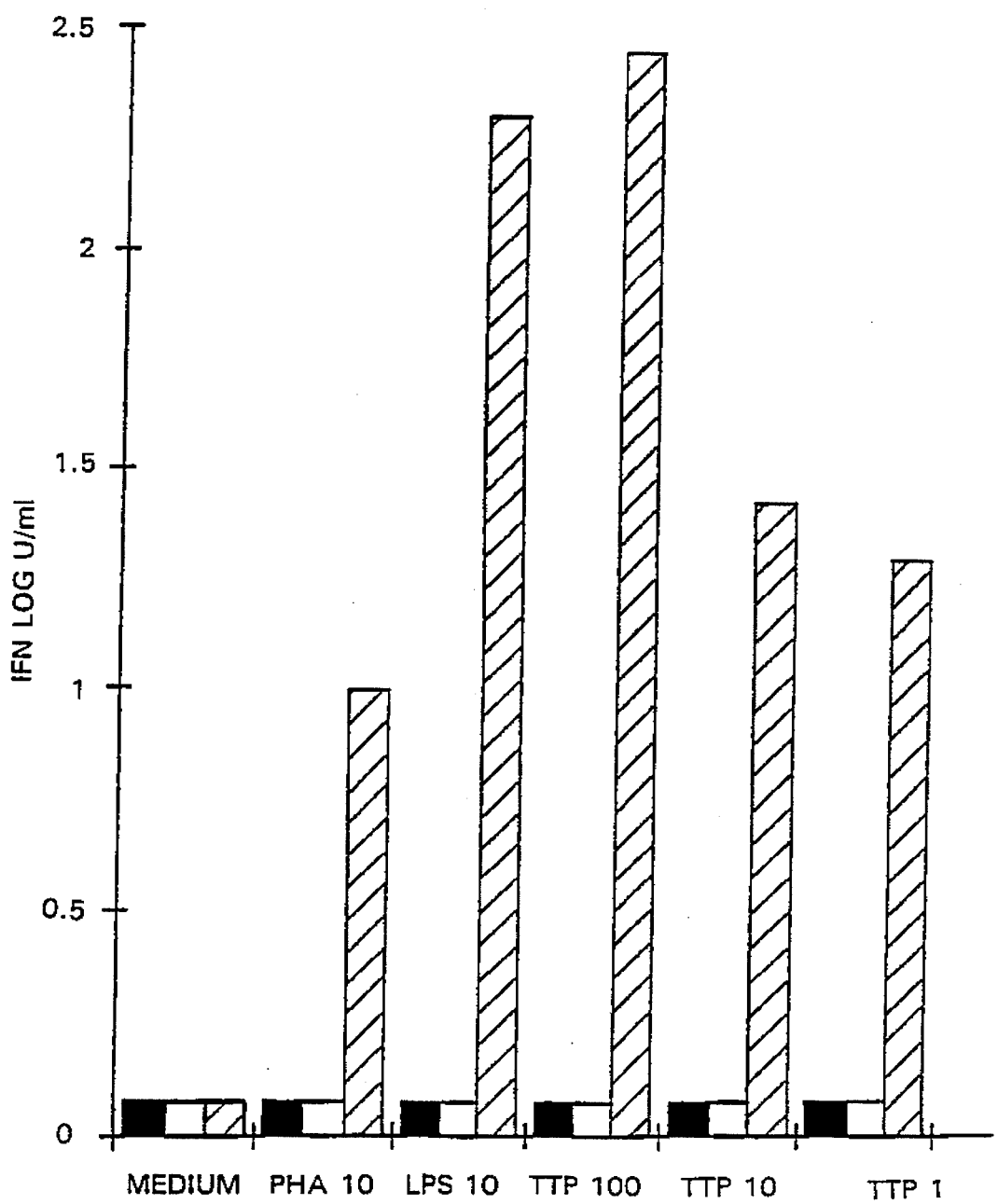

METHOD AND COMPOSITION FOR DETERMINING THE IMMUNOLOGICAL ACTIVITY OF BIOACTIVE SUBSTANCES

The present invention relates to a method and composition for assaying certain bioactive substances and determining their immunological activity with respect to their ability to induce production of cytokines. Cytokines, such as interferons (IFNs) and tumor necrosis factors-(TNFs), are hormone-like proteins which play an important role in virtually all immunological reactions, as well as in the regulatory process responsible for the maintenance of homeostasis. The production of such cytokines can be induced by certain substances which, on account of their bioactive and immunomodulating activity, are useful in the therapy of immunodeficiencies and related diseases.

There is, of course, a substantial need of methods for properly and easily assaying the immunological activity of such bioactive substances. It is the object of the present invention to provide such a method.

The method according to the present invention allows one to determine whether a tested substance is able to induce production of different cytokines and permits a quick and efficient check of the properties of certain substances, namely their immunological activity, at each stage of production, separation, purification and formulation into final compositions. The present invention provides also a composition and kits suitable for carrying out said method.

Tests used until now to determine immunological activity are numerous but difficult to carry out. When a new therapeutical composition having an immunological effect is clinically tested, its immunological effectiveness is evaluated by monitoring the numerous, well known and analytically determinable features of immunological systems employing standard methods. Once the activity is proven, there emerges the necessity for representative single tests enabling a quick check of the status of a patient in terms of his or her immunological response.

In clinical studies, evaluating IFN serum levels may be difficult, unprecise and misleading. Interferons are often produced locally in various tissues, they are short-lived, their action is paracrine (in the immediate vicinity only) and they are strongly bound to cellular receptors and carrier proteins.

On the other hand, technological processes for manufacturing, purification and/or separation of immunologically active substances such as in particular, extracts from raw peat are usually multi-step processes, and there is always the need for establishing a reliable and fast test enabling a thorough control of the production. Moreover, since the substances are frequently of a complex nature, as it is the case with peat extracts, it is important to have a similar test for determining the activity of individual fractions of such substances. It is also necessary to find out a microscale testing method, since the products to be analysed are very costly.

The following four basic findings allowed the inventors to solve the above described problems.

1. Some immunoactive peat extracts induce the production of cytokines, such as interferons and tumor necrosis factors, in in-vitro cultures of peripheral blood leukocytes, the induction being dependent on the dose.

2. Interferon-$\beta$ (and TNF-$\alpha$) is produced in significantly higher quantities by BALB/c mice resident peritoneal cells (RPC) when treated with immunoactive peat extracts as compared to a spontaneous release of these cytokines in non-treated samples.

3. Certain peat extracts, when tested in-vitro as mentioned above show a synergistic effect in combination with known immunomodulators, such as organoselenium compounds, the p-chlorophenylamide of 3-methyl- 5-benzoylamino-isothiazol-4-carboxylic acid and indomethacin. This allows the use of much smaller quantities of immunologically active substances to show their activity.

4. PBL of healthy volunteers treated with TTP (a certain peat-derived product) administered orally at a dosage of 5 mg/day, tested for induction of certain cytokines, IFN-$\alpha$, IFN-$\gamma$ and TNF-$\alpha$, lose the ability to respond to induction of the cytokines with TTP solution after prolonged, uninterrupted administration of TTP orally and regain this ability after approximately two weeks of hiatus.

BRIEF DESCRIPTION OF THE DRAWINGS

FIG. 5 shows the effect of different batches of TTP on IFN production by PBL;

FIG. 6 shows the effect of different batches of TTP on TNF production by PBL;

FIG. 7 shows neutralization of IFN by polyclonal anti-IFN sera; and

FIGS. 8, 9, 10, 11, 12 and 13 show the response of PBL cultures to INF inducers during oral administration of TTP.

Figure 1:
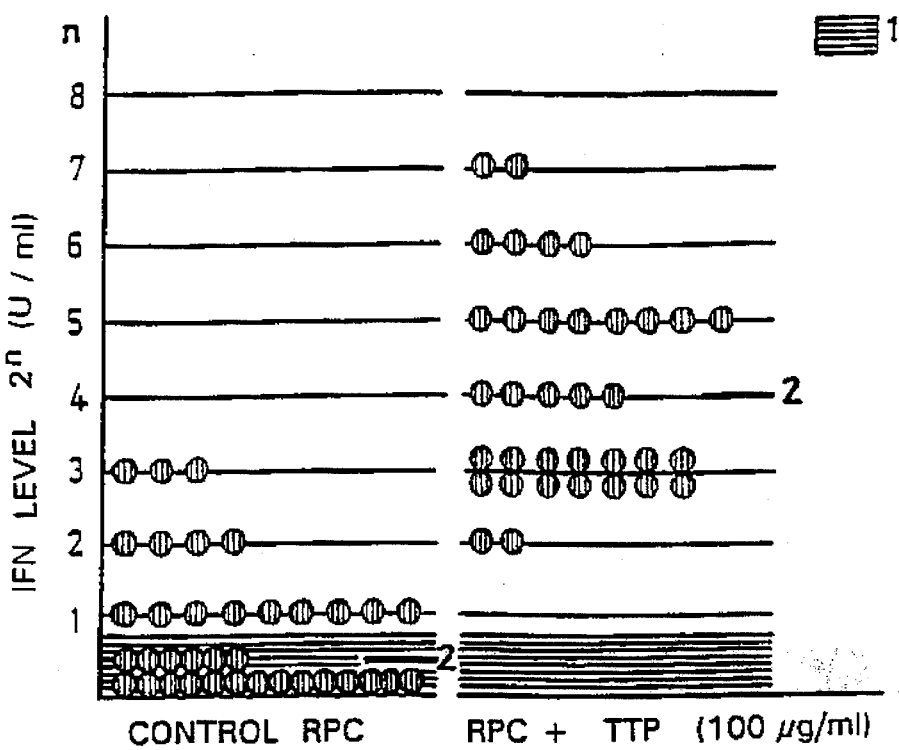
FIG. 1 is a comparison of INF production by RPC with and without TTP.

The method according to the present invention comprises the steps of treating a human peripheral blood leukocyte (PBL) culture or a suspension of BALB/c mice resident peritoneal cells (RPC), with a solution of the substance to be tested in order to induce production of cytokines, and then determining said cytokines according to standard identification methods.

The peripheral blood leukocyte (PBL) culture used according to the first variant or embodiment of the instant method is a short term culture prepared from fresh leukocytes of healthy humans with a nutrient medium suitable for tissue culture. The preferred density of a ready-for-use culture is about $8 \times 10^6$ leukocytes/ml. The solution to be tested is preferably used in a concentration of 0.1–200 µg/ml. The method is, in particular, suitable for testing peat extracts.

A micro-scale determination is possible when the solution to be tested, e.g. a peat extract or a fraction thereof, is admixed with an immunomodulating agent, such as a non-steroidal anti-inflammatory drug, preferably a substance selected from the group comprising organoselenium compounds, such as ebselen, certain isothiazole derivatives, such as the p-chlorophenylamide of 3-methyl-5-benzoylamino-isothiazole- 4-carboxylic acid, and indomethacin, as well as analogs, homologs and metabolites of such substances.

Examples of organoselenium compounds which can be used for this purpose are compounds of the following formulae 1–3; the compound of formula 2 (Ebselen) being preferred:

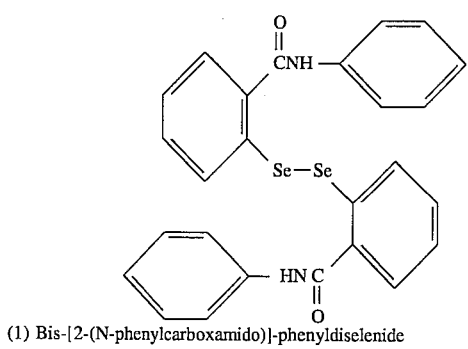

(1) Bis-[2-(N-phenylcarboxamido)]-phenyldiselenide

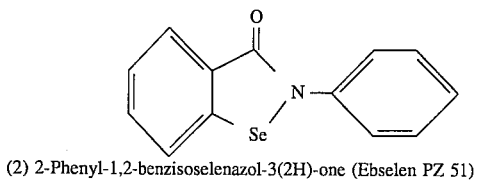

(2) 2-Phenyl-1,2-benzisoselenazol-3(2H)-one (Ebselen PZ 51)

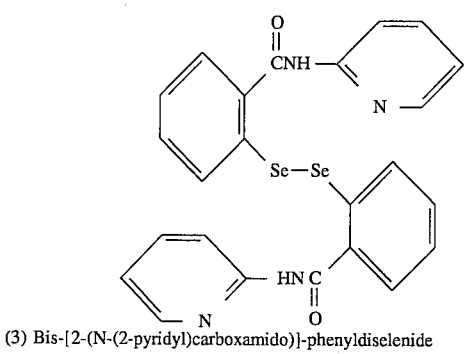

(3) Bis-[2-(N-(2-pyridyl)carboxamido)]-phenyldiselenide

Examples of isothiazole derivatives which can be used for the above purpose are compounds of the general formula I

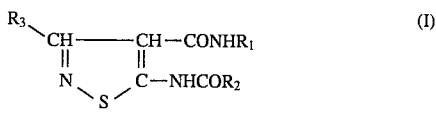

wherein $R_1$ is halophenyl, preferably chlorophenyl, $R_2$ is phenyl and $R_3$ is lower alkyl, preferably methyl. The halogen atom in the halophenyl group, chlorophenyl group $R_1$ is preferably in p-position of the phenyl ring.

The preferred compound of the above formula I is the p-chlorophenylamide of 3-methyl-5-benzoylamino-isothiazole-4-carboxylic acid, i.e. the compound of formula I wherein $R_1$ is p-chlorophenyl, $R_2$ is phenyl and $R_3$ is methyl. For brevity sake, this compound will be referred to below as 'Compound ITCL'. There exists a Trade Mark registration "VRATIZOLIN®" for this compound in Poland. Its synthesis and properties are described in Arch. Immunol. et Ther. Exp. 1973, 21, 891.

All the immunomodulating agents referred to above for being Useful for micro-scale determinations, i.e. the organoselenium compounds, the isothiazole derivatives indomethacin, have in common that they are non-steroidal anti-inflammatories which inhibit the synthesis of prostaglandins. They amplify the test results in the method according to the present invention. For this reason, they are particularly useful for micro-determinations. Amplification of the results may be 5–20 times.

Out of all the various non-steroidal anti-inflammatory compounds useful for the purpose of amplification, seleno organic compound (1, 2 and 3) and compound ITCL, but especially indomethacin, are the preferred ones.

In the instant invention, different antisera, which recognise individual induced cytokines, are employed. These sera are known and used for testing and standardisation of different cytokines. Identification of the induced cytokines should take place at the moment of completion of the cytokine formation and prior to its proteolysis. Among different cytokines induced, some are formed slowly and remain stable in the solution, as for example interferon γ, while others are formed rapidly and are susceptible to proteolysis, as for example tumor necrosis factors.

The method as described above may be employed also for the determination of an immunological response of a human individual to a certain immunoactive substance, provided that such immunological response is not stimulated by other factors, as for example by vital or bacterial infections. It may be applied for monitoring of the drug response in individual patients, for the determination of the optimal dose of a therapeutic cytokine inducer, such as TTP, as well as for the establishment of the effective scheme of the drug administration. The method is based on the assessment of the hyporeactivity state to IFN induction.

Thus, the present invention also relates to a method for determining the immunological response of a human individual to a therapy using a cytokine inducing immunomodulator substance. Said method is characterised in that a peripheral blood leukocyte (PBL) culture of the human individual treated with such immunomodulator substance, is treated in defined time intervals with a solution of the substance administered in order to induce production of cytokines, which are then determined according to standard methods (including ELISA assays of cytokines), in order to determine the moment of development of hyporeactivity to the substance after prolonged administration of the substance and the moment of regaining the ability to respond to an additional dose of the substance after a certain period of hiatus.

The time intervals are preferably about 7–14 days.

In a preferred embodiment, the above method is applied in the course of a therapy using a peat extract as cytokine inducing immunomodulator substance.

According to a particularly preferred embodiment of the invention, this method is applied in the course of a therapy using TTP as cytokine inducing immunomodulator substance, said TTP being, inter alia, the subject of PCT application No. PCT/EP92/00491, (and the corresponding U.S. application Ser. No. 07/849,490) wherein said TTP, its characteristics and its production are described in detail. TTP is a water soluble peat-derived bioactive product containing not more than 70% by weight sodium chloride based on dry mass. The following is the published abstract of said PCT application:

The peat-derived bioactive product contains not more than 70%, preferably not more than 60% by weight of inorganic salts, especially of sodium chloride, based on dry solids. It is obtainable by a process wherein a highly concentrated aqueous solution of inorganic salts, especially of sodium chloride containing peat-derived bioactive ingredients is diluted with demineralized water and subjected to reverse osmosis in order to desalinate the solution, inorganic salts being removed, and wherein the resulting solution is concentrated and clarified, and, optionally, in at least one further step, sterilized and/or spray-dried. A pharmaceutical formulation containing a peat-derived bioactive product, in the form of a gel, is prepared by combining a sterile alcoholic menthol solution; the resulting mixture is gradually combined with colloidal silica to convert the liquid composition into gel form, the weight ratio of liquid mixture to silica preferably being from 90:10 to 94:6. A cosmetic preparation such as a gel, ointment, balm, shampoo, bath salt lotion, etc. contains as active ingredient the instant peat-derived bioactive product in a quantity of 0.01–10% by weight, preferably 0.05–1% by weight, more preferably 0.05–0.1% by weight.

In view of the above, the instant invention also relates to TTP, whenever used, tested or determined according to the methods of the instant invention.

The present invention also provides, in its second variant, for a testing method which is suitable for quick monitoring of technological processes for the production, purification, separation or the like of the immmunoactive substances. For instance, when a suspension of BALB/c mice resident peritoneal cells (RPC) is treated with the solution to be tested, mice interferon-$\beta$ as well as tumor necrosis factor are induced. Both may be detected and qualitatively determined according to standard identification methods. In this method, a suspension of fresh mouse resident peritoneal cells (RPC), containing approx. $1\times10^6$ cells/ml is used. The solution to be tested is prepared in a nutrient medium Eagle, or RPMI-1640 with the addition of 10% of fetal calf serum. The results obtained are evaluated against a calibration curve prepared with a model substance. As a model substance, a sample of the same immunologically active substance tested in a traditional way may be used. Again, the method is particularly suitable for monitoring the process for obtaining peat extracts as well as analysing their fractions.

The instant method is very simple and efficient in comparison with other known methods, because it is based on a direct induction of interferon $\beta$ instead, as is the case in a number of conventional tests, of a secondary effect of formulation of antibodies. Until now, it was not possible to find any similar method due to the fact that the immunosystem of mice significantly differs from the human immunosystem and tests recognised as indicative for human immunologic response, such as the presence of interferons in the tissues of spleen or lymphonodes etc., do not work with the best laboratory test animals, i.e. with mice of BALB/c type.

It was now found that a clear immunological response of the BALB/c mice can be obtained when resident peritoneal cells (RPC) are chosen as a biological material for testing, fresh suspensions of such cells being used. For each test it sufficient to sacrifice just three animals. Results are obtained within several hours. The biological material may also be cultured and a corresponding line of macrophages be established.

The method according to the present invention employs the use of biological material, namely a peripheral blood leukocyte (PBL) culture or a suspension of BALB/c mice resident peritoneal cells (RPC), according to the information given above. Presence and concentration of each cytokine is determined by methods for testing and standardisation of interferons known from "Methods in Enzymology", 1986, vol.119, part C: "Interferon", edited by Sidney Pestka. Determination of the whole spectrum of cytokines induced identifies the immunological status of a patient.

For the proper evaluation of the results, it is essential that the biological material for carrying out both variants of the method according to the present invention is selected from the proper donors. In case of human leukocytes, samples taken from individuals who show a hypo-reactivity (rare cases), i.e. a low level of immunological response, should be excluded from the evaluation. In case of the BALB/c mice RPC suspension, samples taken from additionally stimulated animals (for example infected ones) should also be excluded from the evaluation. In case of the BALB/c mice RPC suspensions, samples should not be taken from too young or from too old animals, as there is an age-dependent deficiency in cytokine production in such mice. 5–8 weeks old healthy animals should be selected. Samples showing very high spontaneous production of cytokines should be eliminated, especially when immunoregulatory substances are tested, since no potentiation of cytokine induction or sometimes even reduction of such induction may be observed.

That embodiment of the method according to the present invention, wherein amplification of the results is achieved by admixing a non-steroidal anti-inflammatory drug (one of the substances referred to above, such as compound ITCL or seleno organic compounds 1, 2, and 3, but preferably indomethacin) to the solution to be tested, is a microscale test, particularly suited for determining the induced TNF and IFN activity. This test is economic, fast, applicable for assaying a great number of samples simultaneously and suitable for standardization and, at least partial automatization.

The two variants of the method according to the present invention are described by way of example in more detail below:

Preparation of the solution of the substance to be tested:
The substance to be tested, e.g. a peat extract, is dissolved in sterile bidistilled water at a concentration of 10 mg/ml. The samples are sterilized by filtration through 0.45 µm, 600 kPa max Millipore(R), antibacterial filters. Next, solutions are made in a complete RPMI-1640 medium containing heat-inactivated fetal bovine serum (FBS).

A) The PBL variant

Cytokine induction

Buffy coats from healthy blood donors may be obtained from the regional transfusion center. Alternatively, peripheral blood leukocytes (PBL) may be isolated from heparinized venous blood of healthy volunteers by Ficoll-Hypaque® (or Bistopaque®) density gradient (g=1.077) centrifugation, with subsequent twice washing of the cells. The erythrocytes were lysed with $NH_4Cl$ treatment according to Cantell et al. (Cantell, K., Hirvonen, S., Kauppinen, H. L.: Production and Partial Purification of Human Immune Interferon. Meth. Enzymol. 119, 54, 1988). The leukocytes from a single donor containing approximately $8\times10^6$ leukocytes/ml in RPMI 1640 medium supplemented with 10% fetal bovine serum (FBS), L-glutamine and antibiotics were used. All lots of FBS were pretested. Only non-mitogenic FBS for PBL cultures was used. The cytokine inducers were added to 200–1000 µl volumes of the cultures. The reference cytokine inducers were phytohemagglutinin (PHA) (Pharmacia Fine Chemicals, Sweden or Sigma, USA). The induced cultures of PBL were incubated in an atmosphere of 5% $CO_2$ in air at 37° C. for 20 h and centrifuged. Supernatants were stored at 4° C. and assayed for IFN activity within one week. Supernatants for TNF activity determination have to be stored at −90° C. or in liquid nitrogen to avoid inactivation due to proteolysis.

Interferon assay

Confluent monolayers of A549 cells were prepared in microplates in Dulbecco-modified Minimum Essential Medium (DMEM), with 10% PBS, L-glutamine, and antibiotics (penicillin 100 units/ml and streptomycin 100 µg/ml ). IFN samples diluted in the plates were added to the cell monolayer and incubated at 37° C. for 20 h in 5% $CO_2$ in air. The cells were then washed and challenged with encephalomyocarditis virus (EMCV). The titer of IFN was defined as the dilution of IFN sample that reduced virus cytopathogenic effect by 50% after 48 h of incubation. The MTT (3-[4.5-dimethylthiazol-2-yl]-2,5-diphenyltetrazolium bromide) method (Hansen, M. B., Nielsen, S. E. and Berg. K.: Re-examination and Further Development of a Precise and Rapid Dye Method for Measuring Cell Growth/Cell Kill. J. Immunol. Meth. 1989, 119, 203–210) to measure the cell kill in the ELISA scanner was also used. Laboratory standards of IFN have to be included in all assays e.g. recombinant human IFN-γ (specific activity $2\times10^6$ units/mg), the natural human leukocyte IFN-α ($3\times10^6$ IU/ml) and IFN-γ ($2\times10^6$ IU/ml).

TNF assay

The cytotoxic activity of TNF was measured in $L_{929}$ cells according to Flick and Gifford (Flick, D. A., Gifford, G. E.: Comparison of in Vitro Cell Cytotoxic Assays for Tumor Necrosis Factor. J. Immunol. Meth. 68, 1667, 1984). The samples and actinomycin D (5 μg/ml) solution were added to monolayer cultures of the cells. After incubation at 37° C. for 20 h, cytotoxic effects of TNF were determined either by the microscopic examination of the cultures or by using the MTT method. The amount causing approximately 50% destruction of the cell cultures was defined as one unit of TNF activity. Comparison with a preparation of TNF-α (Genentech Inc., USA) showed that 1 unit in the assays was equal to 100–200 pg/ml TNF.

Cytokine neutralization assays

The cytokines produced by PBL treated with the examined preparations may be identified by neutralization assays with the specific antibodies (Inglot et al., Organoselenides as potential immunostimulants and inducers of interferon gamma and other cytokines in human peripheral blood leukocytes, Experientia 1990, 46, 308–311). Furthermore, various ELISA kits for the determination of the immunoactivity of a defined cytokine may be applied.

Comment

In the supernatants obtained from the cultured lymphoid cells, other than TNF or IFN cytokines may be found and identified by other standard methods, e.g. Interleukins (IL-1–10), GM-CSF, TGF-β etc.

B) The RPC variant: Cytokine induction

Mouse resident peritoneal cells (RPC) are obtained from approximately 6 weeks old BALB/c mice killed with ether, by injecting into the peritoneal cavity 5 ml of complete RPMI-1640 medium at room temperature. The washing medium containing RPC is collected into ice-cooled 50 ml centrifuge tubes. The RPC are neither washed nor centrifuged. The cells are counted in a Bürker hemocytometer and suspended to a density of $1-1.5\times10^6$ cells/ml. Such cell density is required for all of the assays measuring the effects of various concentrations of the preparation (from 0.1–500 μg/ml). The negative and positive controls are included in all of the tests. The negative control measures the spontaneous release of TNF or IFN by RPC incubated with the complete RPMI-1640 medium without the inducers, whereas the positive control shows the effect of a standard lipo-polysaccharide inducer (LPS from E. coli 055:85, Sigma 1–10 μg/ml). All of the cultures are incubated at 26° C. for 20 h. Thereafter, the cultures are centrifuged at 1000 rpm for 10 min and supernatants are collected. Using an automatic pipette, the supernatants are diluted from 1:2 to 1:256.

Bioassays of the cytokines

To determine TNF activity in supernatants from RPC cultures, the 20 h old monolayer of $L_{929}$ cell cultures are used.

The mouse fibroblast-like $L_{929}$ cells, $2\times10^4$ cells per well in 100 μl of complete medium, are seeded in 96-well flat bottom plates and incubated for 20 h at 37° C. in order to obtain a monolayer.

The transfer of supernatants must be very accurate. The incubation of the $L_{929}$ cultures is carried on for 24 h at 37° C. in an atmosphere of 5% $CO_2$ in air.

Evaluations

1) Reading of the cytotoxic effects under the reverse microscope.

2) MTT test (3-[4.5-dimethylthiazol-2-yl]-2,5-diphenyltetrazolium bromide, Sigma).

To measure cell killing with $L_{929}$ cell cultures, 25 μl of MTT dye solution at a concentration of 5 mg/ml are added into every well of the microplates.

Next, the plates are incubated for 2 h at 37° C. in an atmosphere of 5% $CO_2$ in air.

Thereafter, 100 μl of the solvent solution containing 45 ml of dimethylformamide, 13.5 g of SDS (sodium dodecyl sulphate), and 55 ml of distilled water, are added to every well.

Incubation is carried on for 12 hrs at 37° C. in an $CO_2$ incubator. The results of MTT color test are read in a Multiskan 340/CC reader (Labsystem) using a 570 nm filter. Reference recombinant TNF-α has to be used.

Interferon bioassay

IFN is assayed by inhibition of the cytopathic effect caused by mouse encephalomyocarditis virus (EMCV in mouse $L_{929}$ cells, reference Mu IFN α/β, standard from National Institute of Health Bethesda, Md., USA is included). The cytopathic effect is observed under a reversed microscope and also it is measured by the MTT method as described below:

MTT method according to Berg et al. Berg K., Hansen M. B. and Nielsen S. E. (1990): A new sensitive bioassay for precise quantification of interferon activity as measured via the mitichondrial dehydrogenase function in cells (MTT-method). APMIS, 98, 156–162.

MTT (3/4,5-dimethyl-thiazol-2-yl/2,5-diphenyl tetrazolium bromide, Sigma) is diluted in PBS at a concentration of 5 mg/ml. To measure cell killing with $L_{929}$ cultures, 25 μl of MTT dye solution at a concentration of 5 mg/ml is added to every well of the microplates. The control reference sample of TNF or IFN is included. Next, the plates are incubated for 2 hrs at 37° C. in an atmosphere of 5% $CO_2$ in air. Thereafter, 100 μl of a solution containing 45 ml dimethylformamide, 13.5 g of SDS (sodium dodecyl sulfate) and 55 ml of distilled water are added to every well. After overnight incubation at 37° C. the optical densities at 570 nm are measured, using a microplate reader Start Fax Awareness Technology Inc. 2100, employing the extraction buffer as the blank.

Both TNF-α, IFN-β, and other cytokines, may be also assayed using commercial ELISA kits.

A composition for carrying out the method of the present invention is essentially characterized in that it contains double processed tissue culture water, a culture medium and sera completing the culture medium as well as the human PBL or mice RPC.

A diagnostic kit (cytokine inducer kit) for use in the PBL variant of the present method (for 10–20 manual assays) may contain the following items:

1) Double processed tissue culture water, 100 ml

2) Histopaque® or Ficoll-Hypaque®—1077, (density gradient medium), 100 ml

3) RPMI-1640-Medium, 2×100 ml (with sodium bicarbonate and L-glutamine, sterile filtered, endotoxin tested)

4) Fetal bovine serum (FBS), 20 ml, low in endotoxin and hemoglobin

5) Lectin from *Phaseolus vulgaris* 0.5 mg (Phytohemagglutinin—PHA-P)
6) Round bottom tubes with caps, polypropylene sterile for tissue cultures 17×100 mm, capacity 14 ml, 25 per bag
7) Tissue culture plates with lids, 2 plates, 96 well, flatbottom, sterile.

Reagents available from: Sigma Chemical Co., St. Louis, Mo., USA or other companies.

Such a PBL kit may be used as so-called second phase screening system, to confirm results obtained with RPC cells or sometimes as a direct screening system for several substances which may be inactive as immunomodulators in rodents, e.g. organoselenium compounds.

A diagnostic kit (cytokine inducer kit) for use in the RPC variant of the present method (for 10–20 manual assays) may contain the following items:

1) Double processed tissue culture water, 100 ml
2) RPMI-1640-medium, 2×100 ml, (with sodium bicarbonate and L-glutamine), sterile, filtered, endotoxin tested)
3) Fetal bovine serum (FBS), 20 ml, low in endotoxin and hemoglobin
4) Lipopolysaccharide (LPS) 0.5 mg, from *E. coli* 01.27:B8
5) Round bottom tubes with caps, sterile, 25 per bag, Polypropylene, for tissue culture, 12×75 mm, 6 ml capacity
6)

Tissue culture plates with lids, 5 plates, 96 well, flat bottom, sterile.

Reagents are available from Sigma Chemical Co. St. Louis, Mo., USA or other companies.

A composition for carrying out the method of the present invention involving amplification of the results, which composition is particularly suited for micro-scale tests, is essentially characterised inn that it contains on the one hand a PBL culture or an RPC suspension, and on the other hand a non-steroidal anti-inflammatory drug, preferably a substance selected from the group of organoselenium compounds, such as ebselen, indomethacin or Compound ITCL, and derivatives, analogs, homologs and metabolites of these compounds, most preferably indomethacin.

The following specific Examples illustrate the present invention. It is understood that they do not limit the scope of the invention in any way.

EXAMPLE 1

Individual solutions of RPC were obtained from 36 female, 7-8 weeks old BALB/c mice killed with ether, by injecting into the peritoneal cavity 5 ml of Eagle's minimum essential medium (EMEM), supplemented with 10% heat-inactivated calf serum. Washings from the individual mice contained $1-2\times10^6$ cells/ml. Suspensions of the cells from each mouse were divided into two samples distributed to two tubes. One sample was treated with 100 μg TTP/ml and the other served as a negative control showing spontaneous release of cytokines.

All cultures were incubated at 26° C. for 20 h and thereafter they were centrifugated at 1000 rpm for 10 min. The supernatants were collected and assayed for IFN-β activities in a bioassay using a micromethod of inhibition of cytopathic effect caused by EMCV (encephalomyocarditis virus) in mouse $L_{929}$ cells. In each assay, an internal laboratory standard was included which had been calibrated against the international reference preparation of Mu IFN, G002-904-511, NIH, Bethesda, USA. The cytopathic effect was measured by the MTT method according to Berg et al, APMIS, 98, 156–162. The results obtained were as follows: for the controls the IFN-β level was 1–8 U/ml average being<2, for the samples treated with TTP, the IFN-β level was 4–127 U/ml, the average being 16 U/ml. The results are graphically presented on the accompanying drawing FIG. 1 (Comparison of IFN-β production by RPC treated with TTP and nontreated. 1-limit of detection, 2-mediana. According to Mediana test P=0,0000. Every point shows the level of IFN in RPC isolated from individual mice).

EXAMPLE 2

Figure 2:
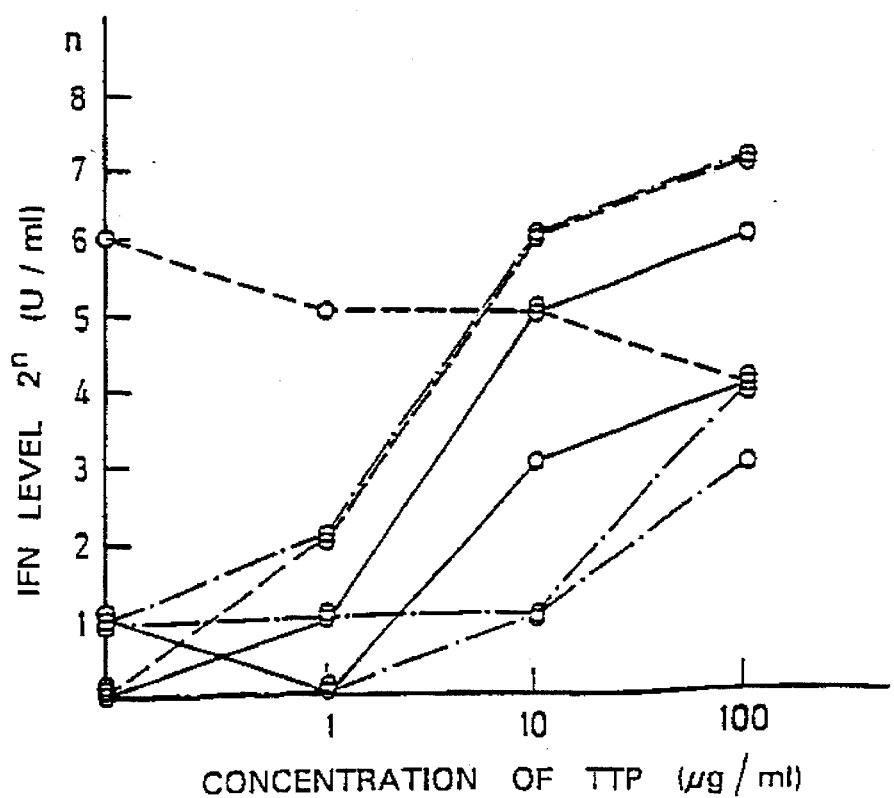
FIG. 2 shows the dependence of IFN production on TTP concentration.

The procedure as described in Example 1 was repeated with a group of 7 mice, however, instead of dividing each individual mouse RPC suspension into two samples, only one suspension was divided into four samples. The samples were distributed to 4 tubes (1 ml in each). One of the samples was a negative control and the remaining three were treated with 100, 10 and 1 μg TTP/ml to determine a TTP dose-dependance of the IFN-β release. After incubation of the cultures for 24 h at 26° C. the tubes were centrifugated. In the collected supernatants IFN-β was determined as described in Example 1. The results obtained are presented on the accompanying drawing FIG. 2 (Dependence of IFN production on TTP concentration). Each curve relates to the results observed with a single mouse derived RPC suspension.

EXAMPLE 3

The procedure as described in Example 1 was followed, except that TNF-α was determined instead of IFN-β.

Figure 3:
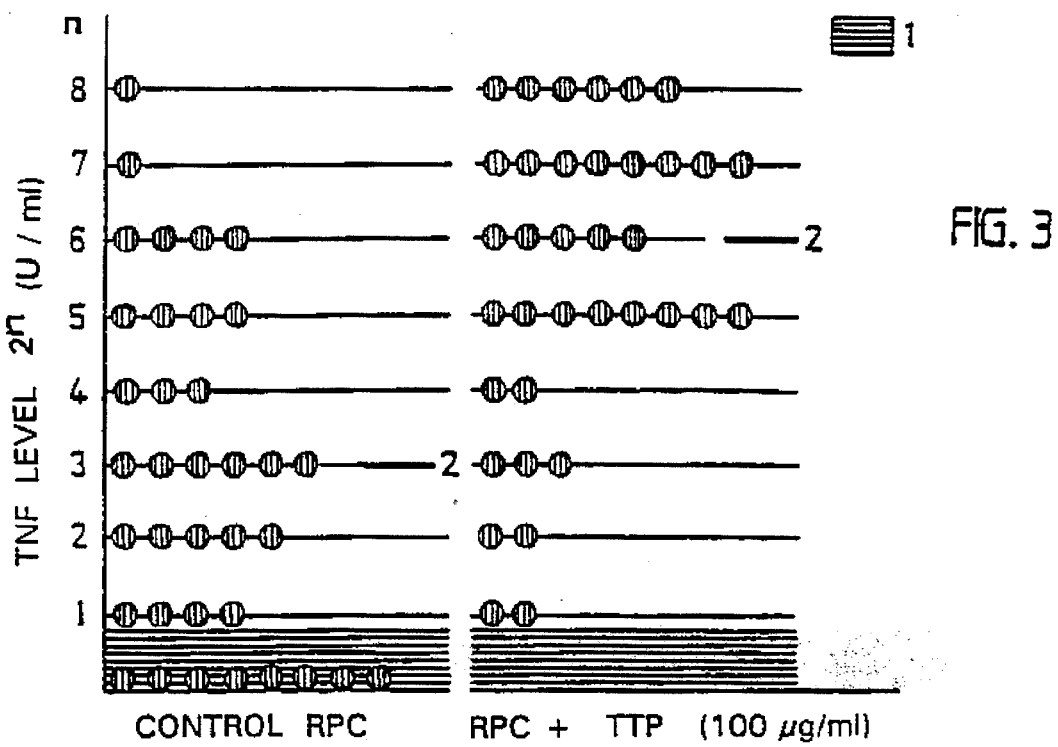
FIG. 3 shows a comparison of TNF production by RPC treated and untreated with TTP.

Supernatants from the RPC cultures, non-treated and treated with 100 μg TTP/ml were assayed for TNF activity in a bioassay. The mouse fibroblast-like $L_{929}$, cells ($4\times10^4$ cells per well in 100 μl of complete EMEM) were seeded in 96-well flat bottom plates (Falcon, Linbro, Flow) and incubated for 4 h at 37° C. in an atmosphere of 5% $CO_2$ in air. The samples were diluted in EMEM with actinomycin D (end concentration 2.4 μg/ml) in the additional plate. Next, the culture medium above the $L_{929}$ cells monolayer was removed and the prepared dilutions were transferred to this culture using a multichannel pipette. After incubation for 20 h at 37° C., the cultures were assayed for cell kill by the MTT method as described above. The results obtained were as follows: for negative controls the TNF-α level was within a range of 1–256 U/ml the average being 8 U/ml, and for the samples treated with TTP the TNF-α level was 2–256 also, but the avenge was 64 U/ml. The results obtained are shown on the accompanying drawing FIG. 3 (Comparison of TNF-α production by RPC treated with TTP and nontreated. 1—limit of detection, 2—mediana. According to Mediana test P=0,0030. Every point shows the level of TNF in RPC isolated from individual mice).

EXAMPLE 4

The procedure as described in Example 2 was followed, except that instead of IFN-β, TNF-α was determined essentially as described in Example 3 above.

Figure 4:
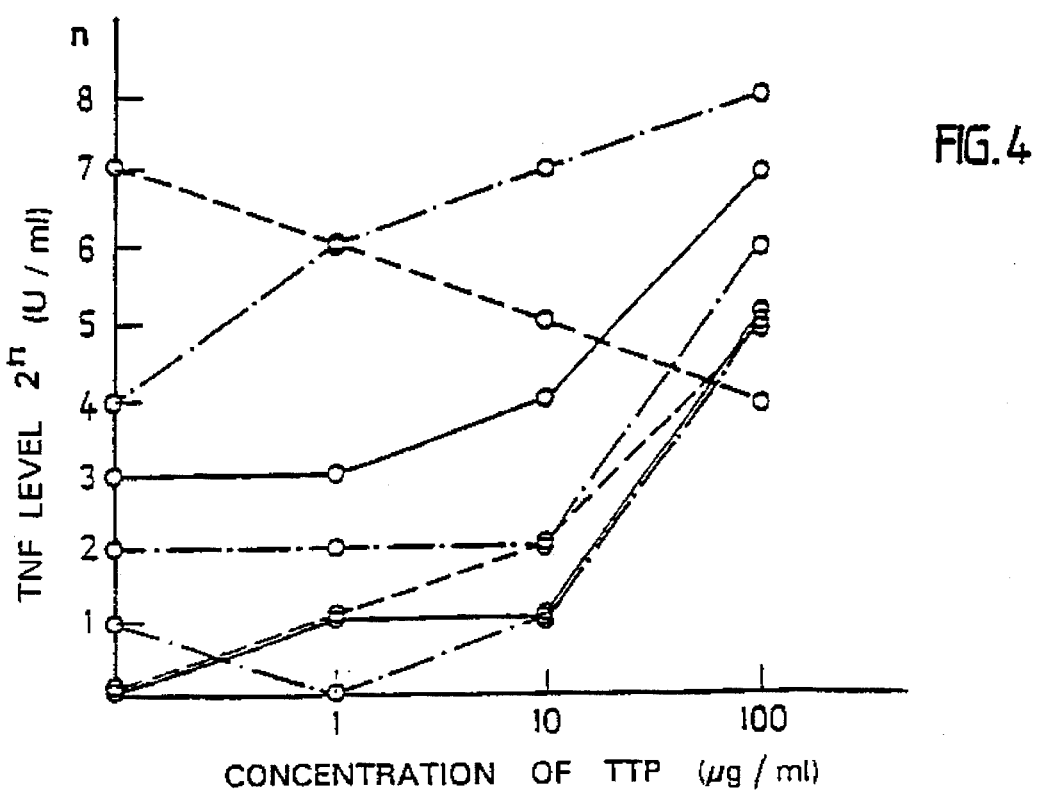
FIG. 4 shows the dependence of TNF production on TTP concentration.

The results obtained are shown on the accompanying drawing FIG. 4 (Dependence of TNF production on TTP concentration).

EXAMPLE 5

A. Biological material. Over 115 buffy coats from individual healthy blood donors, obtained from Wroclaw Regional Transfusion Center, have been used for the assays. The characteristics of the donors are given in a Table 1, below.

TABLE 1

Characteristics of donors of blood used as a source of PBL

| Age (years) | No. | Male | Female | Donation Multiple | Single |
|---|---|---|---|---|---|
| 21–30 | 24 | 22 | 2 | 24 | — |
| 31–40 | 45 | 44 | 1 | 45 | — |
| 41–59 | 46 | 44 | 2 | 40 | 6 |
| Total | 115 | 110 | 5 | 109 | 6 |
| % | 100 | 96 | 4 | 95 | 5 |

The majority of them were young males who donated blood many times. Considerable variations in the response of PBL from the individual donors have been observed and are reported in Table 2 below.

As it results from Table 2, 10–30% of PBL cultures may not respond to a 100 μg/ml TTP dose, whereas only 7% cannot be stimulated by a 10 μg/ml PHA dose, and 20% did not respond to a 10 μg/ml LPS dose with IFN production, and 50% did not respond to the same dose of LPS with TNF production. These data are essential for proper selection of biological material. Non-responding PBL cultures are detected by evaluation of the negative (non-treated, spontaneous release of Cytokine) and positive (treated with a standard inducer, such as PHA or LPS) controls.

TABLE 2

IFN and TNF response of PBL from individual blood donors after stimulation either with various batches of TTP or with standard inducers

| Inducer | Dose (μg/ml) | No. PBL tested | No. IFN (%) | responders to: TNF (%) |
|---|---|---|---|---|
| TTP 010391 | 100 | 19 | 13 (68) | 13 (68) |
|  | 30 | 13 | 6 (46) | 9 (69) |
|  | 10 | 15 | 14 (93) | 13 (87) |
| TTP 020391 | 100 | 14 | 10 (71) | 11 (79) |
|  | 30 | 12 | 8 (67) | 8 (67) |
|  | 10 | 10 | 5 (50) | 5 (50) |
| TTP 101091 | 100 | 26 | 21 (81) | 20 (77) |
|  | 30 | 20 | 9 (45) | 8 (40) |
|  | 10 | 24 | 14 (58) | 15 (63) |
| TTP 010991 | 100 | 5 | 5 (100) | 4 (80) |
|  | 30 | 4 | 2 (50) | 0 (0) |
|  | 10 | 5 | 2 (40) | 3 (60) |
| TTP 021091 | 100 | 5 | 4 (80) | 4 (80) |
|  | 30 | 4 | 3 (75) | 4 (100) |
|  | 10 | 5 | 3 (60) | 3 (60) |
| TTP 111191 | 100 | 5 | 3 (60) | 4 (80) |
|  | 30 | 4 | 2 (50) | 3 (75) |
|  | 10 | 5 | 4 (80) | 2 (40) |
| TTP (8x) | 100 | 29 | 19 (66) | 10 (34) |
|  | 30 | 24 | 14 (58) | 11 (46) |
|  | 10 | 21 | 16 (76) | 2 (10) |
| PHA | 10 | 69 | 64 (93) | 54 (78) |
| LPS | 10 | 41 | 33 (80) | 21 (51) |
| None | — | 69 | 36 (52) | 20 (29) |

TABLE 3

Induction of IFN or TNF by different batches of 100 μ/ml peat extract in International Activity Units

| Series No. | IFN/units/ml | | | TNF/units/ml | | | | |
|---|---|---|---|---|---|---|---|---|
| | Number of assays | Range | Median | Number of assays | 24 h Range | Median | 6 days Range | Median |
| Control without induces | 333 | <10–100 | 10 | 41 | 9–750 | 27 | 9–80 | 9 |
| 31090 | 3 | 5–30 | 30 | 3 | ND | ND | 9–80 | 80 |
| 291290 | 21 | 10–3000 | 100 | 14 | ND | ND | 9–750 | 40 |
| 010391 | 23 | 10–2000 | 60 | 17 | ND | ND | 9–160 | 9 |
| 020391 | 19 | 10–1000 | 30 | 32 | 9–750 | 200 | 9–250 | 27 |

The conditioned media were stored at 4° C. before assaying

Human peripheral blood leukocytes from healthy blood donors ($8 \times 10^6$ cells/ml) were used.

B. Experiments performed

Peat extract samples taken from different production batches numbered as shown in Table 3 have been tested using the PBL test as described above. In the experiments, interferon (IFN) and tumor necrosis factor (TNF) have been determined qualitatively and according to the above mentioned standard procedure; their activity, as expressed in International Activity Units, was determined. Experiments were repeated a number of times quoted in Table 3. Result ranges and medians are also given.

For illustration purposes, a similar test was carried out with a standardised peat preparation. At a concentration of 30 μg/ml, interferon activity was within a range of 30–300 International Activity Units, while at a concentration of 100 μg/ml, it was 300–1000 International Activity Units.

Intermediate concentrations showed a linear relation between dose and response.

The immunoactive peat extracts tested in the above Example are products described in PCT Application No. PCT/EP92/00491.

From the data given in Table 3 it is clear that in PBL cultures negative and positive control is essential for evaluation of the results.

Further experiments show that, when non-responding PBL cultures are not taken into consideration and statistical evaluation of the large number of experiments is performed, the effectiveness of the tests according to the invention cannot be questioned.

For over two years the cytokine inducing activity of over 20 different batches of TTP was determined, including 10 standard commercial batches of the drug, the activity of which has been determined in biological assays, 2) batches rejected by the manufacturer due to the inadequate biological activity determined in mice which was below the established standard and 3) laboratory peat extracts prepared on a small scale. The results obtained are presented in Table 4 below in the form of mean levels of IFN and TNF induced (with calculated standard deviations—SD and statistical significance).

TABLE 4

Effects of different batches of TTP on IFN and TNF production by human PBL

| Inducer | Dose (µg/ml) | IFN | TNF |
|---|---|---|---|
|  |  | $\log_{10}$ units/ml (±SD) | |
| TTP 010391 | 100 | 1.41 ± 1.07[b] | 1.26 ± 0.91[c] |
|  | 30 | 0.96 ± 1.07 | 1.25 ± 0.88[b] |
|  | 10 | 1.81 ± 0.58[c] | 1.45 ± 0.63[c] |
| TTP 020391 | 100 | 1.23 ± 0.81[a] | 1.35 ± 0.75[c] |
|  | 30 | 1.12 ± 0.90 | 1.14 ± 0.83[b] |
|  | 10 | 0.75 ± 0.76 | 0.86 ± 0.90 |
| TTP 101091 | 100 | 1.70 ± 0.91[c] | 1.38 ± 0.81[c] |
|  | 30 | 0.99 ± 1.12 | 0.62 ± 0.80 |
|  | 10 | 1.22 ± 1.07[a] | 0.94 ± 0.76[b] |
| TTP 010991 | 100 | 2.24 ± 0.30[c] | 1.35 ± 0.73[b] |
|  | 30 | 1.00 ± 1.00 | 0.0 |
|  | 10 | 0.56 ± 0.68 | 0.88 ± 0.73 |
| TTP 021091 | 100 | 1.72 ± 0.87[b] | 1.49 ± 0.84[b] |
|  | 30 | 1.39 ± 0.81 | 1.79 ± 0.20[c] |
|  | 10 | 1.11 ± 0.91 | 1.01 ± 0.84 |
| TTP 111191 | 100 | 1.36 ± 1.12 | 1.18 ± 0.62[b] |
|  | 30 | 1.00 ± 1.00 | 1.21 ± 0.71[a] |
|  | 10 | 1.56 ± 0.86[a] | 0.54 ± 0.66 |
| TTP (8x) | 100 | 1.04 ± 0.82[a] | 0.63 ± 0.91 |
|  | 30 | 0.88 ± 0.81 | 0.75 ± 0.84 |
|  | 10 | 1.10 ± 0.70[b] | 0.13 ± 0.40[a] |
| PHA | 10 | 2.08 ± 0.79[c] | 1.67 ± 0.99[c] |
| LPS | 10 | 1.36 ± 0.80[c] | 0.97 ± 1.01[b] |
| None | — | 0.64 ± 0.63 | 0.42 ± 0.67 |

Mean values were calculated from all results of IFN or TNF titrations. The non-responders were regarded as O.

[a-c] Different from "None" (spontaneous production of the cytokine) at [a] $p<0.05$, [b] $p<0.01$ or [c] $p<0.001$. Mediana values corresponding to the results presented in Table 4 are given in the next Table 5, while selected data are presented in a graphic form on FIG. 5 and 6 showing the effects of different batches of TTP on IFN and TNF production, respectively.

TABLE 5

Effect of different batches of TTP on IFN and TNF production by human PBL

| Inducer | Dose (µg/ml) | IFN | TNF |
|---|---|---|---|
|  |  | Units/ml[1] | |
| TTP 010391 | 100 | 30 | 27 |

TABLE 5-continued

Effect of different batches of TTP on IFN and TNF production by human PBL

| Inducer | Dose (µg/ml) | IFN | TNF |
|---|---|---|---|
|  |  | Units/ml[1] | |
|  | 30 | <10 | 27 |
|  | 10 | 100 | 27 |
| TTP 020391 | 100 | 30 | 50 |
|  | 30 | 30 | 34 |
|  | 10 | <10 | <9 |
| TTP 101091 | 100 | 100 | 34 |
|  | 30 | <10 | <9 |
|  | 10 | 45 | 18 |
| TTP 010991 | 100 | 300 | 27 |
|  | 30 | <10 | <9 |
|  | 10 | <10 | 18 |
| TTP 021091 | 100 | 100 | 27 |
|  | 30 | 60 | 80 |
|  | 10 | 60 | 27 |
| TTP 111191 | 100 | 100 | 18 |
|  | 30 | <10 | 40 |
|  | 10 | 100 | <9 |
| TTP (8x) | 100 | 20 | <9 |
|  | 30 | 10 | <9 |
|  | 10 | 20 | <9 |
| PHA | 10 | 200 | 80 |
| LPS | 10 | 30 | 27 |
| None | — | 10 | <9 |

Mediana values were calculated from all results of IFN or TNF titrations.

Identification of the induced cytokines has been performed by means of neutralisation of IFN and TNF induced by TTP.

The above results of the experiments are explained by FIG. 5 and 6 respectively.

Effects of different batches of TTP on IFN production by human PBL (FIG. 5). Seven different batches of TTP were used. Every point of the graph refers to the PBL of an individual healthy blood donor. IFN activity refers to antiviral units. The shaded area shows the limit of the non-significant data. The horizontal lines show mean values. The induction of IFN by 30 and 100 µg/ml of TTP is statistically significant (at $p<0.05$).

Effects of different batches of TTP on TNF production by human PBL. TNF activity is expressed in the cytotoxic units for the mouse $L_{929}$ cells. The response to 30, 100 and 200 ||g/ml of TTP is significant (at $p<0.05$) (FIG. 6).

In the experiments, potent polyclonal antisera have been used, namely: anti-natural IFN-α, anti-lymphoblastoid (Namalwa) IFN-α and anti-natural IFN-γ to neutralize antiviral activity in supernatants of PBL cultures treated for 20 h with three different batches of TTP. Results, as shown on accompanying drawing FIG. 7 (Results of neutralization of IFNs by polyclonal Anti-IFNs sera) indicate that portions of IFN types α and γ produced by PBL from the individual blood donors varied considerably. It is suggested that the released IFN pattern of the each PBL donor is an individual characteristic of the donor.

Neutralisation assays carried out with a potent polyclonal rabbit anti-TNF-α serum (Genzyme Inc.) showed that the TMF induced with TTP is mainly TNF type α. It has been confirmed by the results of similar neutralisations carried out with rabbit polyclonal anti-TNF-β serum (Genzyme Inc.) which did not neutralise the TTP induced TNF activity.

FIG. 7 shows the results of neutralization of IFNs by polyclonal anti-IFNs sera. IFN containing media from PBL cultures incubated with TTP (three different batches of TTP and seven different PBL were used) were treated with the indicated anti-IFN sera. 1—Non treated preparations; 2—Treated with anti-HuIFN-β; 3—Treated with anti-BuIFN-Ly; 4—Treated with anti-Hu/FN-γ.

EXAMPLE 6

The procedure described in Example 5 was followed in order to show the amplifying effect of the presence of an amplifyer, viz. indomethacin, according to the present invention.

Each PBL culture was divided into several samples. One of them was a negative control showing spontaneous release of cytokines, the other one was a positive control treated with a standard potent cytokine inducer of a nature indicated below and the remaining samples were treated with 1–100 µg/ml TTP, batch no. 010391 or 020391, as well as TTP I and TTP II which appear in Tables 6b and 6c respectively, and 5 µg/ml indomethacin+TTP of the same batches (Table 6a) or 10 µg/ml compound ITCL+TTP of the same batches (Table 6b), or else 10 or 20 µg/ml seleno-organic compounds (1), (2) or (3) as defined above+TTP of the same batches. In the supernatants of the incubated cultures IFN and TNF were determined.

The results obtained are shown in Tables 6a, b and c below.

TABLE 6a

The effect of amplification of the cytokine induction in the presence of indomethacin

| Exp. | Inducer | Indo-methacin | Concentration µg/ml | Cytokines (units/ml) | |
|---|---|---|---|---|---|
| | | | | IFN | TNF |
| 1.[a)] | TTP 010391 | – | 100 | 300 | 750 |
| | " | – | 10 | 30 | 250 |
| | " | – | 1 | 20 | 80 |
| | " | + | 100 + 5 | 1000 | 2200 |
| | " | + | 10 + 5 | 200 | 750 |
| | " | + | 1 + 5 | <10 | 250 |
| | LPS | – | 10 | 200 | 500 |
| | none | – | – | <10 | 9 |
| | none | + | 5 | 20 | 27 |
| 2.[b)] | TTP 020391 | – | 100 | 600 | 50 |
| | " | – | 40 | 20 | 9 |
| | " | – | 20 | 10 | 9 |
| | " | – | 10 | <10 | <9 |
| | " | + | 100 + 5 | 600 | 80 |
| | " | + | 40 + 5 | 100 | 27 |
| | " | + | 20 + 5 | 100 | 9 |
| | " | + | 10 + 5 | 30 | 9 |
| | PHA | – | 5 | 600 | 50 |
| | PHA | + | 5 + 5 | 2000 | 80 |
| | none | – | – | 60 | <9 |
| | none | + | 5 | 10 | <9 |

[a)]PBL were prepared from fresh heparinized blood by Ficoll-Hypaque separation technique. PBL cultures contained $7 \times 10^6$ cells/ml,
[b)]PBL were prepared from the buffy coat obtained from the Regional Transfusion Center. The cells were processed according to the Cantell et al. method (Meth. Enzymol. 1981, 78, 29–38). PBL cultures contained $8 \times 10^6$ cells/ml.

TABLE 6b

The effect of amplification of the cytokine induction in the presence of Compound ITCL

| Exp. | Inducer | Compound ITCL | Concentration | Cytokines (units/ml) | |
|---|---|---|---|---|---|
| | | | | IFN | TNF |
| 1. | TTP 010391 | – | 100 | 100 | 18 |
| | TTP 010391 | – | 30 | 100 | 9 |
| | TTP 010391 | + | 100 + 10 | 3000 | 80 |
| | TTP 010391 | + | 30 + 10 | 300 | 80 |
| | PHA | – | 10 | 3000 | 250 |
| | none | – | – | 10 | <9 |
| | none | + | 10 | <10 | <9 |
| 2. | TTP I | – | 100 | 3000 | 27 |
| | TTP I | – | 30 | 30 | <9 |
| | TTP I | + | 100 + 10 | 3000 | 250 |
| | TTP I | + | 30 + 10 | 300 | 9 |
| | PHA | – | 10 | 100 | 18 |
| | none | – | – | 10 | <9 |
| | none | + | 10 | 10 | <9 |

TABLE 6c

The effect of amplification of the cytokine induction in the presence of the seleno-organic compounds

| Exp. | Inducer | Seleno-organic compounds | Concentration µg/ml | Cytokines (units/ml) | |
|---|---|---|---|---|---|
| | | | | IFN | TNF |
| 1. | TTPs | — | 10 | 100 | <9 |
| | TTPs | — | 5 | 10 | <9 |
| | TTPs | Comp. (1) | 10 + 20 | 300 | 27 |
| | TTPs | Comp. (1) | 5 + 20 | 100 | 27 |
| | TTPs | Comp. (2) | 10 + 20 | 300 | 50 |
| | TTPs | Comp. (2) | 5 + 20 | 100 | 9 |
| | PHA | — | 10 | 100 | <9 |
| | none | Comp. (1) | 20 | 200 | 9 |
| | none | Comp. (2) | 20 | 100 | 27 |
| | none | — | — | 10 | <9 |
| 2. | TTP II | — | 50 | 10 | <9 |
| | TTP II | — | 5 | 10 | <9 |
| | TTP II | Comp. (3) | 50 + 10 | 30 | 27 |
| | TTP II | Comp. (3) | 10 + 10 | 30 | 27 |
| | PHA | — | — | 30 | <9 |
| | none | Comp. (3) | 10 | 10 | <9 |
| | none | — | — | 10 | <9 |

PBL cultures contained $8 \times 10^6$ cells/ml. TTP is a peat preparation produced on a small scale. The relatively low TNF response is probably due to the fact that the buffy coats were stored for 20 hrs at 4° C. before the preparation of the cultures. The seleno-organic compounds are inducers of the cytokines as well as TTP.

EXAMPLE 7

A diagnostic test reflecting the effect of administration of TTP orally in daily doses of 5 mg in the form of commercially available tablets on PBL in vitro culture response to an additional dose of TTP induction of cytokines was performed according to the particulars given below:

The test was performed with 4 healthy female volunteers, age 43–58, who donated 20 ml venous blood taken from vulnaris weekly, before, during and after the administration of TTP at a daily dose of 5 mg in tablets. Two different regimen of administration have been performed. Two of the volunteers (referred to further as B. K. and J. Z. J.) were subjected to a treatment with TTP consisting of three seven-day cycles: the drug was administered per os, one 5 mg tablet daily for one week with a seven day rest followed by a seven-day period of TTP oral administration. The total dosage was 21 tablets. The other two volunteers (referred to further as A. D. I. and W. F.) were treated with one 5 mg TTP tablet daily administered per os continuously for three weeks. The total dosage was also 21 tablets. After two weeks of rest, the treatment was repeated.

The 5 mg. TTP tablets used were a standard commercial product of TORF CORPORATION Pharmaceutical Factory of Wroclaw, Poland. Each tablet contained 5 mg TTP, 43 mf Lactose and 2 mg MYVATEX. To induce cytokines in PBL in vitro cultures, powdered TTP as a pure substance was used in form of a stock solution containing 20 mg TTP/ml of pyrogen free redistilled water stored at 4° C.

Blood samples taken from the volunteers were heparinised with Heparin POLFA solution without preservatives at a final concentration of 10 units/ml and treated as described earlier to prepare a PBL in vitro culture, which was then treated with cytokine inducers PHA, LPS and TTP in a manner described in the preceding examples. 200 μg cultures were used in each treatment. The supernatants were stored at 4° C. and assayed for IFN within one week, and stored at $-20°$ C. and assayed, respectively for TNF to avoid inactivation due to spontaneous proteolysis.

IFN and TNF were assayed in the same manner as described above. The results obtained are presented on the accompanying drawings FIGS. 8–13 (response of PBL cultures of different patients to IFN inducers and to TNF inducers during the oral administration of TTP).

As may be seen from the data presented on FIGS. 8 and 9 showing the IFN response of the first group of volunteers during administration cycle, the response declined and returned to the initial value after two weeks rest. In contrast, TNF response shown on FIGS. 10 and 11 increased during administration of TTP and returned to the normal level after two weeks rest.

Data shown on FIGS. 12 and 13 reflecting the response to the cytokine induction in the other way of administration of volunteer A. D. I. prove that the hyporeactivity state to IFN induction is reached after 3 weeks of continuous administration of TTP orally. The hyporeactivity state shown as loss of ability of PBL cultures to respond to the induction of IFN with TTF solution disappears after two weeks of rest. In contrast, during three weeks of TTP administration, the hyporeactivity to TNF induction did not develop (FIG. 12).

The above results indicate that the optimum dose of immunomodulator being a cytokine inducer can be established individually for each patient treated with a simple PBL test according to the present invention.

We claim:

1. A method for determining the immunological activity of a cytokine inducing substance which is a peat extract or a fraction thereof, comprising treating a reagent selected from the group consisting of:
   a) a human peripheral blood leukocyte (PBL) culture from a non-mitogenic nutrient medium suitable for tissue culture and obtained from a donor not hyporeactive to production of a cytokine, and
   b) a suspension of 5–8 week old BALB/c mice resident peritoneal cells (RPC) which have not been immunologically stimulated and do not exhibit spontaneous production of a cytokine at a level which interferes with determination of other production of said cytokine,
   with a solution of a substance which is a peat extract or fraction thereof to induce the production of said cytokine and then determining the presence of said cytokine.

2. A method according to claim 1, wherein the cytokine determined is interferon or tumor necrosis factor.

3. A method according to claim 1, wherein said solution has a concentration of 0.1–200 μg of said substance per ml.

4. A method according to claim 1, wherein said reagent is a ready-for-use culture of a) with a cell density of about $8\times10^6$ leukocytes/ml or a ready-for-use culture of b) with a cell density of about $1-2\times10^6$ cells/ml.

5. A method according to claim 1, wherein said solution comprises a nutrient medium selected from the group consisting of Eagle and RPMI-1640 with an addition of 10% of non-mitogenic fetal calf serum.

6. A method according to claim 1 in which said extract is a water soluble peat-derived bioactive product containing not more than 70% by weight sodium chloride based on dry mass.

7. A method according to claim 1, wherein a synthetic, non-peptide amplifier is added to said solution.

8. A method according to claim 7, wherein said amplifier is a non-steroidal anti-inflammatory and prostaglandin-synthesis inhibiting drug.

9. A method according to claim 8, wherein said amplifier is the p-chlorophenylamide of 3-methyl-5-benzoylaminoisothiazole-4-carboxylic acid, 2-phenyl-1,2-benzisoselenazol-3(2H)-one or indomethacin.

10. A composition for carrying out the method of claim 1, comprising a human peripheral blood leukocyte culture from a non-mitogenic nutrient medium suitable for tissue culture obtained from a donor not hyporeactive to production of said cytokine, a cytokine inducing substance which is peat extract or a fraction thereof and a non-mitogenic nutrient medium suited for tissue cell culture.

11. A composition according to claim 10, further comprising a synthetic non-peptide amplifier.

12. A composition according to claim 11, in which said amplifier is a non-steroidal anti-inflammatory and prostaglandin-synthesis inhibiting drug.

13. A composition according to claim 12, in which said amplifier is selected from the group consisting of compound p-chlorophenylamide of 3-methyl-5-benzoylaminoisothiazole- 4-carboxylic acid, 2-phenyl-1,2-benzisoselenazol-3(2H)-one and indomethacin.

14. A composition for carrying out the method of claim 1, comprising a suspension of 5–8 week old BALB/c mice resident peritoneal cells which have not been immunologically stimulated and do not exhibit spontaneous production of a cytokine at a level which interferes with determination of other production of the cytokine, a peat extract or fraction thereof and a non-mitogenic nutrient medium suited for tissue cell culture.

15. A composition according to claim 14, further comprising a synthetic non-peptide amplifier.

16. A composition according to claim 15, in which said amplifier is a non-steroidal anti-inflammatory and prostaglandin-synthesis inhibiting drug.

17. A composition according to claim 16, in which said amplifier is selected from the group consisting of compound p-chlorophenylamide of 3-methyl-5-benzoylaminoisothiazole- 4-carboxylic acids, 2-phenyl-1,2-benzisoselenazol-3(2H)-one and indomethacin.

18. A method for determining the immunological response of a patient in the course of a therapy with a cytokine inducing substance which is peat extract or a fraction thereof, comprising:
   a) subjecting a patient to repeated treatment with a substance which is a peat extract or fraction thereof,
   b) obtaining a peripheral blood leukocyte (PBL) culture from said patient,
   c) adding a solution of said substance to said PBL culture to induce interferon, and d) determining said interferon.

19. A method according to claim 18 in which said peat extract is a water soluble peat-derived bioactive product containing not more than 70% by weight sodium chloride based on dry mass.

20. A method for determining the immunological activity of a cytokine inducing substance which is a peat extract or fraction thereof comprising treating a suspension comprising 5–8 week old BALB/c mice resident peritoneal cells which have not been immunologically stimulated and do not exhibit spontaneous production of a cytokine at a level which interferes with determination of other production of said cytokine, with a solution of a substance which is a peat extract or fraction thereof to induce the production of said cytokine and then determining the presence of said cytokine.

21. A method for the treatment of a patient in need of immunosystem stimulating therapy comprising the steps of
 (a) repeatedly administering a cytokine inducing substance to a patient;
 (b) determining whether a cytokine selected from the group consisting of interferon and tumor necrosis factor has been induced;
 (c) determining whether human peripheral blood leukocytes obtained from said patient are hyporeactive to interferon induction by said cytokine inducing substance;
 (d) interrupting the administration of said substance for a given period of time;
 (e) determining whether the human peripheral blood leukocytes of said patient have regained the ability to respond to said cytokine inducing substance at the end of said period of time; and
 (f) restarting the administration of said cytokine inducing substance to said patient.

22. The method of claim 21, wherein step (a) is effected for about two to three weeks and the given period of time in step (d) is about one to two weeks.

23. The method of claim 21 in which the leukocytes are in a nutrient medium at a cell concentration of about $8 \times 10^6$ cells/ml.

24. The method of claim 21, wherein said cytokine inducing substance is a peat extract or a fraction thereof.

25. The method of claim 24, in which said extract is a water-soluble peat-derived bioactive product containing not more than 70% by weight sodium chloride based on dry mass.

* * * * *